(12) United States Patent
Lee et al.

(10) Patent No.: US 11,357,999 B2
(45) Date of Patent: Jun. 14, 2022

(54) ELECTRONIC DEVICE

(71) Applicant: LG Display Co., Ltd., Seoul (KR)

(72) Inventors: JungHyoung Lee, Daejeon (KR); Jaemin Moon, Seoul (KR); Jina You, Seoul (KR)

(73) Assignee: LG DISPLAY CO., LTD., Seoul (KR)

(*) Notice: Subject to any disclaimer, the term of this patent is extended or adjusted under 35 U.S.C. 154(b) by 5 days.

(21) Appl. No.: 16/727,300

(22) Filed: Dec. 26, 2019

(65) Prior Publication Data
US 2020/0391047 A1  Dec. 17, 2020

(30) Foreign Application Priority Data

Jun. 11, 2019 (KR) .................. 10-2019-0068705

(51) Int. Cl.
*A61N 5/06* (2006.01)
*F21V 9/38* (2018.01)
(Continued)

(52) U.S. Cl.
CPC .............. *A61N 5/0616* (2013.01); *F21V 9/38* (2018.02); *A61N 2005/0632* (2013.01);
(Continued)

(58) Field of Classification Search
CPC .......... A61N 5/0616; A61N 2005/0632; A61N 2005/0663; A61N 2005/0653;
(Continued)

(56) References Cited

U.S. PATENT DOCUMENTS

| 8,038,822 | B2* | 10/2011 | Kindler | H04N 9/3129 |
| | | | | 156/245 |
| 2006/0139580 | A1* | 6/2006 | Conner | G02B 27/0994 |
| | | | | 353/98 |

(Continued)

FOREIGN PATENT DOCUMENTS

| CN | 205182009 U | 4/2016 |
| CN | 109842977 A | 6/2019 |

(Continued)

OTHER PUBLICATIONS

Chinese Office Action dated Nov. 17, 2021 issued in corresponding Patent Application No. 201911053099.0 w/English Translation (16 pages).

*Primary Examiner* — Brian T Gedeon
*Assistant Examiner* — Joshua Andrew Schum-Houck
(74) *Attorney, Agent, or Firm* — Polsinelli PC

(57) ABSTRACT

An aspect of the present disclosure relates to an electronic device, and more particularly, to an electronic device that may include: a substrate; a plurality of light emitting devices, disposed on the substrate; a wavelength converting layer, disposed on the substrate, wherein the plurality of the light emitting devices emit a light of same color, wherein light emitted from the light emitting devices is converted by going through the wavelength converting layer, wherein the converted light is extracted to outside of the electronic device, and has a wavelength longer than that of the light emitted from the light emitting devices. Through this, an electronic device can be provided emitting light having a wavelength from which effects of inflammation treatments and skin regeneration can be acquired.

19 Claims, 12 Drawing Sheets

(51) Int. Cl.
*F21W 131/20* (2006.01)
*F21Y 115/15* (2016.01)

(52) U.S. Cl.
CPC ............... *A61N 2005/0647* (2013.01); *A61N 2005/0653* (2013.01); *A61N 2005/0663* (2013.01); *F21W 2131/20* (2013.01); *F21Y 2115/15* (2016.08)

(58) Field of Classification Search
CPC .... A61N 2005/0647; A61N 2005/0667; F21V 9/38; F21W 2131/20; F21Y 2115/15
See application file for complete search history.

(56) References Cited

U.S. PATENT DOCUMENTS

| | | | | |
|---|---|---|---|---|
| 2007/0217473 A1* | 9/2007 | Abe | ............... | H01S 3/0627 372/50.124 |
| 2011/0163659 A1* | 7/2011 | Lang | ............... | H01L 51/5262 313/498 |
| 2011/0306922 A1* | 12/2011 | Khan | ............... | C04B 35/6264 604/20 |
| 2012/0126268 A1* | 5/2012 | Seo | ............... | F21V 5/045 257/98 |
| 2012/0267745 A1* | 10/2012 | Tsuji | ............... | H01L 27/14627 257/432 |
| 2013/0092965 A1* | 4/2013 | Kijima | ............... | F21V 29/83 257/98 |
| 2016/0027862 A1* | 1/2016 | Lee | ............... | H01L 51/5209 257/40 |
| 2017/0246474 A1* | 8/2017 | Schanze | ............... | A61N 5/0616 |
| 2018/0159071 A1* | 6/2018 | Song | ............... | H01L 51/5246 |

FOREIGN PATENT DOCUMENTS

| | | |
|---|---|---|
| JP | 2011-096171 A | 5/2011 |
| JP | 2015-115241 A | 6/2015 |
| WO | 2015/083940 A1 | 6/2015 |

\* cited by examiner

ELECTRONIC DEVICE

CROSS REFERENCE TO RELATED APPLICATION

This application claims priority from Korean Patent Application No. 10-2019-0068705 filed on Jun. 11, 2019, which is hereby incorporated by reference in its entirety.

BACKGROUND

Field of the Disclosure

The present disclosure relates to an electronic device.

Description of the Background

Skins can be damaged due to aging of cells, repetition of specific facial expressions, continued exposure to external environments (ultraviolet, fine dusts, and the like), stresses, and the like. For example, aging of cells and repetition of specific facial expressions may cause skin folds, and continued exposure to external environments, stresses, and the like may cause various troubles such as pimples and freckles.

An object of the management of skins for preventing or minimizing such damages in skins is to maintain clean and soft skins having no blemish, and, especially, skin management of faces among body parts has attracted the highest interest. Accordingly, people try to maintain clean skins by getting massages for skin management of faces, applying functional cosmetic products, and using various cleaning products.

Recently, devices that are attached to or worn by user's faces and output light (for example, a mask-type skin management device and the like) have appeared. In such light output devices, a plurality of light sources are disposed, and light can be output toward user's facial skins and the like.

However, development of such electronic devices is in an initial stage, and it is necessary to design the electronic devices in accordance with the necessities of various persons.

SUMMARY

An aspect of the present disclosure provides an electronic device emitting light of wavelengths from which effects of inflammation treatments and skin regeneration can be acquired.

Another aspect of the present disclosure provides an electronic device from which effects of inflammation treatments and skin regeneration can be acquired regardless of an ethnic group and a user's skin thickness.

Yet another aspect of the present disclosure provides an electronic device for skin management or skin treatments that includes a light source having a long life.

An electronic device according to an aspect of the present disclosure may include: a substrate; a plurality of light emitting devices, disposed on the substrate; a wavelength converting layer, disposed on the substrate, wherein the plurality of the light emitting devices emit a light of same color, wherein light emitted from the light emitting devices is converted by going through the wavelength converting layer, wherein the converted light is extracted to outside of the electronic device, and has a wavelength longer than that of the light emitted from the light emitting devices.

The converted light emitted from the wavelength converting layer may have a wavelength of 600 nm to 850 nm.

The wavelength converting layer may include a plurality of wavelength conversion areas that are separated from each other, the converted light emitted from the plurality of wavelength conversion areas has different wavelengths.

A partition wall may be disposed between any two adjacent wavelength conversion areas among the plurality of wavelength conversion areas, and the height of the partition wall may be larger than the thicknesses of the any two adjacent wavelength conversion areas.

The refractive index of the partition wall may be lower than the refractive indexes of the any two adjacent wavelength conversion areas.

The plurality of light emitting devices may be disposed on the front face of the substrate, and the wavelength converting layer may be attached to the rear face of the substrate, the rear face of the substrate may be integrally formed with a plurality of protrusions, and the plurality of protrusions correspond to the light emission areas of the plurality of light emitting devices so as to introduce the light emitted from the light emission areas of the plurality of light emitting devices into the wavelength converting layer.

The adhesion layer may be disposed between the substrate and the wavelength converting layer.

The plurality of light emitting devices include: an auxiliary electrode, disposed on the substrate, and having a mesh shape, the mesh shaped auxiliary electrode forms a plurality of open areas; a first electrode, disposed on the auxiliary electrode and the substrate, and including at least one open area, wherein each open area of the first electrode is located in one open area of the auxiliary electrode and extending along the edge thereof, such that the part of the first electrode inside the open area thereof and the part of the first electrode outside the open area thereof connect to each other through a narrow path; an insulating film, disposed on the auxiliary electrode, and having the plurality of the open areas of the auxiliary electrode exposed, wherein the insulating film covers the at least one open area of the first electrode; an organic layer, disposed on the insulating film and the first electrode; a second electrode, disposed on the organic layer.

The auxiliary electrode may contain a metal material, the first electrode may contain a transparent conductive material, and the second electrode may contain a metal having reflectivity.

The substrate may be formed with a mask shape, and at least a part thereof forms a curved face.

The electronic device may further comprise a front cover and a rear cover, formed with a mask shape that matches the mask shape of the substrate, wherein the substrate, the plurality of light emitting devices and the wavelength converting layer disposed on the substrate are sandwiched between the front cover and the rear cover.

The electronic device may further comprise a wearing device, fastened to the rear cover.

The converted light coming from the wavelength converting layer may irradiate a face of a user wearing the electronic device.

The wavelength of the converted light can penetrate into an inner skin of a user.

The substrate may be made of flexible material, and the substrate may be bended or folded. And, the electronic device may be used for skin cosmetics or skin treatments.

According to aspects of the present disclosure, an electronic device can be provided emitting light of wavelengths from which effects of inflammation treatments and skin regeneration can be acquired.

According to aspects of the present disclosure, an electronic device from which effects of inflammation treatments and skin regeneration can be acquired regardless of an ethnic group and a user's skin thickness can be provided.

According to aspects of the present disclosure, an electronic device for skin management or skin treatments that includes a light source having a long life can be provided.

BRIEF DESCRIPTION OF THE DRAWINGS

The accompanying drawings, which are included to provide a further understanding of the disclosure and are incorporated in and constitute a part of the disclosure, illustrate aspects of the disclosure and together with the description serve to explain the principle of the disclosure.

In the drawings.

DETAILED DESCRIPTION

Figure 1A:
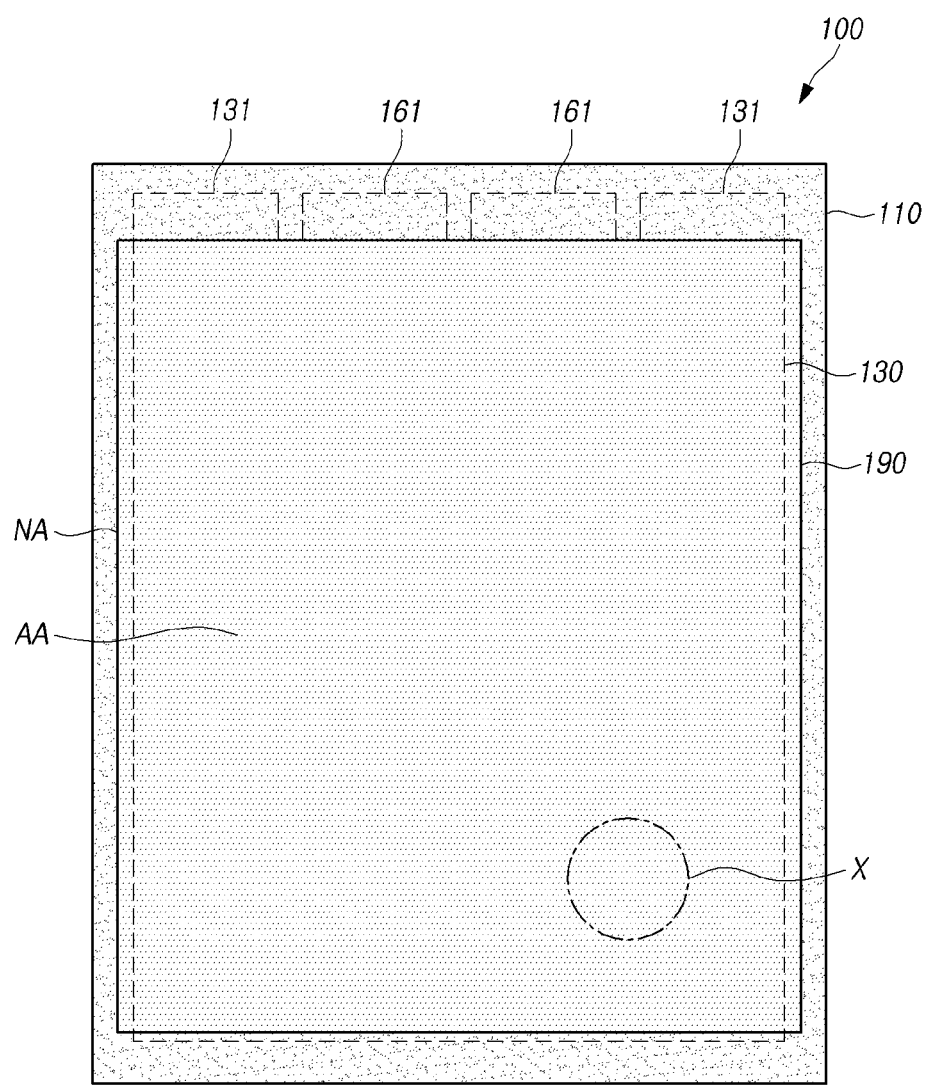
FIG. 1A is a plan view schematically illustrating an electronic device according to an aspect of the present disclosure.

Hereinafter, some aspects of the present disclosure will be described in detail with reference to the accompanying illustrative drawings. In designating elements of the drawings by reference numerals, the same elements will be designated by the same reference numerals although they are shown in different drawings. Further, in the following description of the present disclosure, a detailed description of known functions and configurations incorporated herein will be omitted when it may make the subject matter of the present disclosure rather unclear.

In addition, terms, such as first, second, A, B, (a), (b) or the like may be used herein when describing components of the present disclosure. Each of these terminologies is not used to define an essence, order or sequence of a corresponding component but used merely to distinguish the corresponding component from other component(s). In the case that it is described that a certain structural element "is connected to", "is coupled to", or "is in contact with" another structural element, it should be interpreted that other structural elements may "be connected to", "be coupled to", or "be in contact with" the certain structural element or the another structural element as well as that the certain structural element is directly connected to or is in direct contact with another structural element.

Figure 1B:
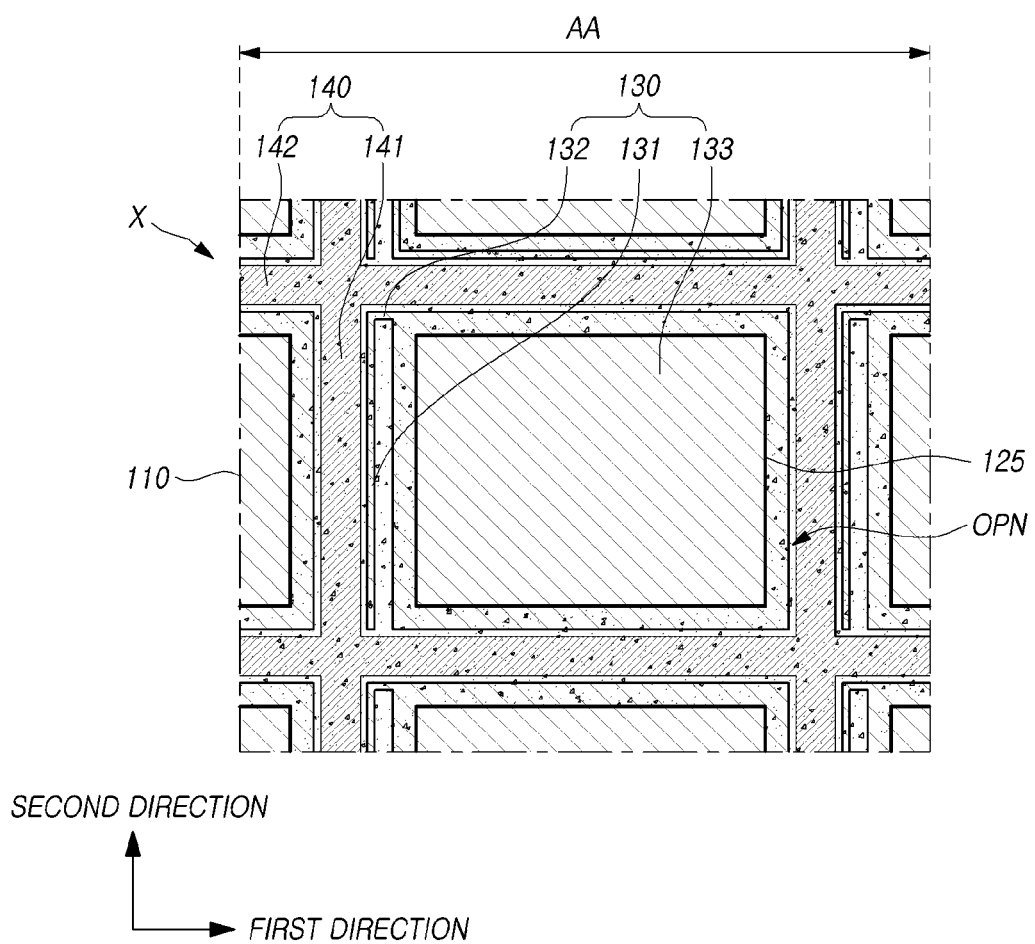
FIG. 1B is a specific plan view of area X illustrated in FIG. 1A.

FIG. 1A is a plan view schematically illustrating an electronic device according to an aspect of the present disclosure. FIG. 1B is a specific plan view of an area X illustrated in FIG. 1A.

Referring to FIGS. 1A and 1B, an electronic device 100 according to an aspect of the present disclosure may include an active area AA in which a plurality of organic light emitting devices OLED are disposed and a non-active area NA disposed on an outer side of the active area AA.

As illustrated in FIG. 1A, the non-active area NA may include a plurality of pad electrodes 131 and 161.

A first electrode 130 of an organic light emitting device OLED disposed in the active area AA extends to the non-active area NA to form a pad electrode 131, and a second electrode of the organic light emitting device OLED also extends to the non-active area NA to form a pad electrode 161. However, the present disclosure is not limited thereto.

For example, an auxiliary electrode 140 illustrated in FIG. 1B extends to the non-active area NA to form a pad electrode, and pad electrodes extending from the auxiliary electrode 140 and the first electrode 130 may be disposed in an overlapping manner.

A plurality of pad electrodes 131 and 161 disposed in the non-active area NA may be electrically connected to the outside. A signal (for example, a DC voltage) may be applied to the organic light emitting device OLED disposed in the active area AA trough the pad electrode in the non-active area NA.

In accordance with application of a signal to the organic light emitting device OLED, the organic light emitting device OLED emits light, and accordingly, light can be output to the outside of the electronic device 100 through the active area AA.

In addition, an encapsulation member 190 that can prevent penetration of moisture and a foreign material may be disposed on the organic light emitting device OLED.

The encapsulation member 190 may be disposed in the active area AA and the non-active area NA.

In description presented below, for the convenience of description, the structure of the active area AA of the electronic device 100 according to the present disclosure will be focused on.

As illustrated in FIG. 1B, the electronic device 100 according to an aspect of the present disclosure includes an auxiliary electrode 140 overlapping with the first electrode 130 of the organic light emitting device OLED.

Referring to FIG. 1B, the auxiliary electrode 140 may be disposed on a substrate 110.

The auxiliary electrode 140 may be in a matrix shape or a mesh shape having a thin width over the entire active area AA. In a case in which the auxiliary electrode 140 is disposed in the mesh shape, an open area of the auxiliary electrode 140 is disposed in a hexagonal shape, an octagonal shape, a circular shape, or the like, and a uniform current can thus be applied to the first electrode 130 of the entire active area AA due to the auxiliary electrode 140, and accordingly, light emission having uniform luminance can be performed by the electronic device 100 having a large area.

The auxiliary electrode 140 may include a plurality of first auxiliary electrodes 141 extending in a first direction and a plurality of second auxiliary electrodes 142 extending in a second direction that is a direction intersecting with the first direction.

Such an auxiliary electrode 140 may include at least one open area in the active area AA.

For example, two first auxiliary electrodes 141 and two second auxiliary electrodes 142 intersect with each other, whereby one open area may be formed.

A part of the first electrode 130 of the organic light emitting device OLED may overlap with the open area formed by the auxiliary electrode 140. Another part of the first electrode 130 may be electrically connected to the auxiliary electrode 140.

The first electrode 130 may include a first part 131 that is electrically connected to the auxiliary electrode 140, a second part 132 that is connected to the first part 131 and extends in a direction different from a direction in which the first part 131 extends, and a third part 133 that is connected to the second part 132 and has a plate shape.

More specifically, the second part 132 may be an area that is connected to the third part 133 and extends in the second direction, and the first part 131 may be an area that is connected to the second part 132 and extends in the first direction.

However, the structure of the electronic device 100 according to an aspect of the present disclosure is not limited thereto. For example, there may be three or more parts that branch from the third part 133 of the first electrode 130 and are connected to the auxiliary electrode 140.

An insulating film 125 that overlaps with the auxiliary electrode 140 and overlaps a part of the first electrode 130 may be disposed.

Here, the insulating film 125 may be composed of an inorganic material such as SiOx or SiNx. However, the present disclosure is not limited thereto, and the insulating film 125 may be composed of an organic material such as a photo-acryl or may be composed of a plurality of layers of an inorganic material and an organic material.

The insulating film 125 may be arranged to overlap with an open area OPN formed in the first electrode 130 and surrounding the third part 133 of the first electrode 130 while overlapping with the auxiliary electrode 140. Here, each open area of the first electrode is located in one open area of the auxiliary electrode and extending along the edge thereof, such that the part of the first electrode inside the open area thereof and the part of the first electrode outside the open area thereof connect to each other through a narrow path. The insulating film 125 may overlap with the first part 131 and the second part 132 of the first electrode 130, and, together with this, the insulating film 125 may overlap with an edge part of the third part 133 of the first electrode 130.

In another aspect, the insulating film 125 may not overlap with a central part of the third part 133.

In this way, while the insulating film 125 disposed in the active area AA is configured to cover the auxiliary electrode 140 and the first electrode 130 disposed above the auxiliary electrode 140, the insulating film 125 is not disposed in a light emission area in which light of the organic light emitting device OLED is emitted.

Particularly, the insulating film 125 of the active area AA is formed to surround the auxiliary electrode 140 and decreases a level difference caused by the auxiliary electrode 140, whereby components formed thereafter can be stably formed without being open-circuited or peeled off.

An organic layer and the second electrode of the organic light emitting device OLED may be sequentially disposed on the substrate 110 in which such an insulating film 125 is disposed. The organic layer may include an area overlapping with the auxiliary electrode 140, the first electrode 130, the insulating film 125, and the second electrode.

The active area AA of the electronic device 100 according to an aspect of the present disclosure having such a planar structure may include a plurality of light emission areas and a plurality of non-light emission areas.

For example, the active area AA may include a first light emission area. The first light emission area may be an area not overlapping with the insulating film 125.

The active area AA may include a first non-light emission area. The first non-light emission area may be an area corresponding to an area in which the insulating film 125 is disposed.

The structure of the active area AA of the electronic device 100 according to an aspect of the present disclosure will be reviewed as below with reference to FIG. 2.

Figure 2:
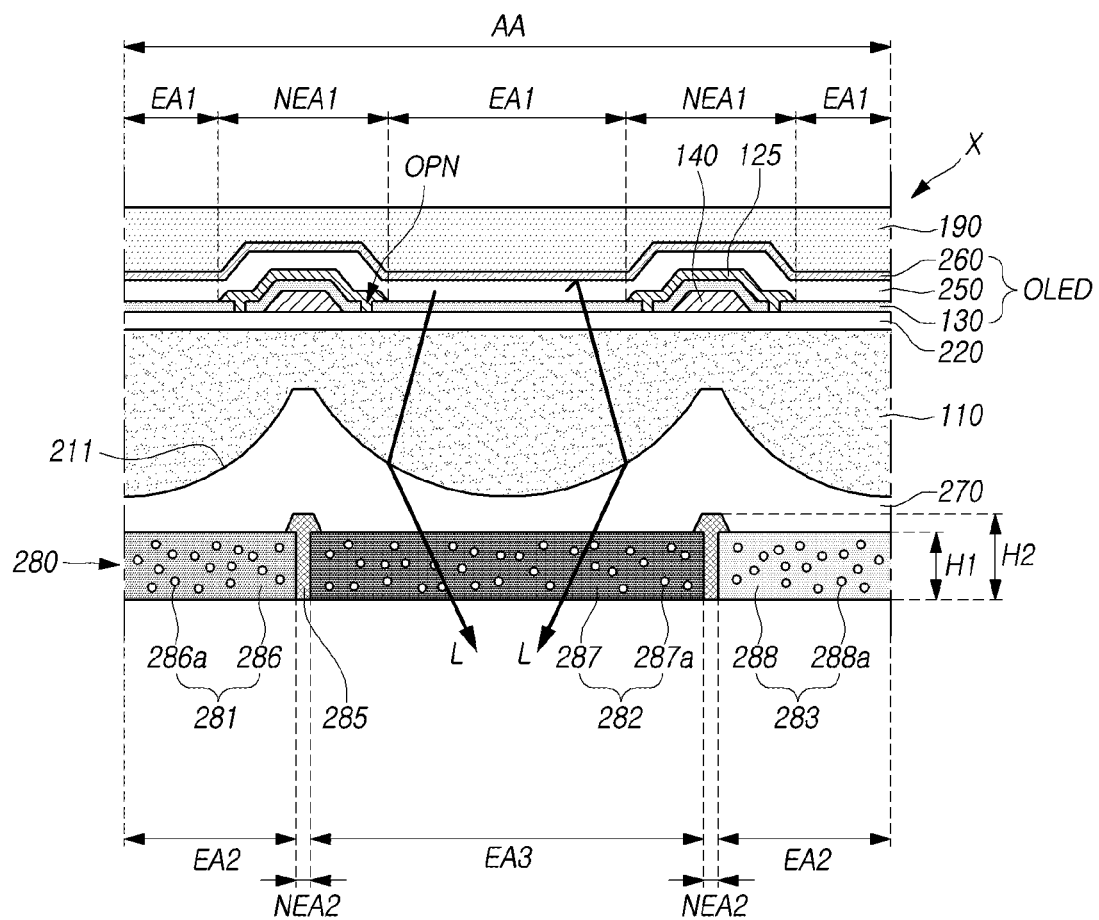
FIG. 2 is a cross-sectional view of area X illustrated in FIG. 1A.

FIG. 2 is a cross-sectional view of the area X illustrated in FIG. 1A, and taken along line I-I' of FIG. 1B.

Referring to FIG. 2, the electronic device 100 according to an aspect of the present disclosure may include: a substrate 110 having a rear face on which a plurality of protrusions are integrally arranged; an organic light emitting device OLED disposed on the substrate 110; and a wavelength converting layer 280 that is disposed on the rear face of the substrate 110 and is included in an area corresponding to the active area AA. However, the present is not limited thereto, in another example, the organic light emitting device OLED and the wavelength converting layer may be arranged on a same side of the substrate.

The electronic device 100 according to an aspect of the present disclosure may be a lighting apparatus including an organic light emitting device OLED. For example, the electronic device 100 may be a cosmetic device or a treatment device including an organic light emitting device OLED.

The substrate 110 may be composed of a flexible material having high transmittance. Accordingly, the electronic device 100 according to an aspect of the present disclosure can be bent or folded.

For example, the substrate 110 may be in the form of a film containing one selected from a group composed of a polyester-based polymer, a silicon-base polymer, an acryl-based polymer, a polyolefin-based polymer, and a copolymer thereof. More specifically, the substrate 110 may contain one selected from a group composed of PET, PBT, polysilane, polysiloxane, polysilazane, polycarbosilane, polyacrylate, polymethacrylate, polymethylacrylate, polymethylmethacrylate, polyethylacrylate, polyethylmethacrylate, COC, COP, PE, PP, PI, PMMA, PS, POM, PEEK, PES, PTFE, PVC, PC, PVDF, PFA, SAN, and a combination thereof.

A buffer layer 220 may be disposed on such a substrate 110.

Although the buffer layer 220 is illustrated to have a configuration of a single layer in FIG. 2, the present disclosure is not limited thereto. For example, the buffer layer 220 may be multiple-buffer layer composed of multiple layers.

The buffer layer 220 may contain an inorganic insulating material. For example, the buffer layer 220 may contain any one of SiOx, SiNx, and SiON. However, the present disclosure is not limited thereto.

A plurality of auxiliary electrodes 140 may be disposed on the buffer layer 220. Although a configuration in which the auxiliary electrode 140 is a single layer is illustrated in FIG. 2, the present disclosure is not limited thereto, and the auxiliary electrode 140 may be multiple layers.

The first electrode 130 of the organic light emitting device OLED may be disposed on the auxiliary electrode 140.

A part of the first electrode 130 may be brought into contact with the auxiliary electrode 140.

The first electrode 130 may contain a material having electric resistance higher than that of the auxiliary electrode 140.

For example, the auxiliary electrode 140 may contain any one of aluminum (Al), gold (Au), copper (Cu), titanium (Ti), tungsten (W), and molybdenum (Mo), and an alloy thereof.

The first electrode 130 may include a transparent conductive material, for example, any one of indium tin oxide (ITO), indium zinc oxide (IZO), and indium gallium zinc oxide (IGZO).

The first electrode 130 is formed using a transparent conductive material and has an advantage of transmitting emitted light and has a disadvantage of having electric resistance higher than that of a non-transparent metal.

Accordingly, a distribution of currents applied to the active area becomes uneven due to high resistance of the transparent conductive material, and such a non-uniform current distribution inhibits uniform-luminance light emission of the electronic device 100.

In the present disclosure, by disposing the auxiliary electrode 140 over the entire active area AA, a uniform current is applied to the first electrode 130 of the organic light emitting device OLED disposed in the active area AA, and there is an effect of uniform luminance of the active area AA of the electronic device 100 having a large area.

In addition, in a case in which a foreign material is inserted into at least one organic light emitting device OLED among a plurality of organic light emitting devices OLED disposed in the active area AA, a voltage is concentrated on the first electrode 130 at a position at which the foreign material is inserted, and voltages applied to the other organic light emitting devices OLED disposed in the active area AA become lower than a drive voltage, and light emission of the organic light emitting devices OLED disposed in the active area AA may not be achieved.

However, an open-circuit or short-circuit reduction effect of the lighting apparatus can be acquired through the structure of the first electrode 130 according to an aspect of the present disclosure.

More specifically, as illustrated in FIG. 2, the first electrode 130 of the organic light emitting device OLED disposed in the active area AA may be brought into contact with the auxiliary electrode 140. As described above, since the resistivity of the first electrode 130 is higher than the resistivity of the auxiliary electrode 140, the first electrode 130 connected to the auxiliary electrode 140 may operate as a resistance component.

Accordingly, even in a case in which a foreign material is inserted into at least one organic light emitting device OLED among the plurality of organic light emitting devices OLED disposed in the active area AA, and a voltage is concentrated on the first electrode 130 at a position at which the foreign material is inserted, the voltage is not different much from voltages applied to the other organic light emitting devices (OLED) disposed in the active area AA, and organic light emitting devices (OLED) into which a foreign material has not been inserted can emit light regardless of the organic light emitting device (OLED) into which the foreign material has been inserted.

The organic light emitting device OLED disposed in an area in which a foreign material is present has high electric resistance due to the foreign material, and a current applied to the organic light emitting device OLED decreases much, whereby the organic light emitting device OLED may not emit light.

To sum up, in the present disclosure, as illustrated in FIG. 2, by bringing the first electrode 130 of the organic light emitting device OLED and the auxiliary electrode 140 into contact with each other, only the organic light emitting device OLED disposed in the area in which the foreign material is present does not emit light, and there is an advantage of improving the life of the lighting apparatus.

An insulating film 125 overlapping with the auxiliary electrode 140 may be disposed on the first electrode 130 of the organic light emitting device OLED having such a structure.

An open area OPN may be formed in an area in the first electrode 130 in which the first electrode 130 and the auxiliary electrode 140 do not overlap with each other. The insulating film 125 may be disposed in the open area OPN.

The insulating film 125 is formed to surround the auxiliary electrode 140 and decreases a level difference caused by the auxiliary electrode 140, whereby components formed thereafter can be stably formed without being open-circuited or peeled off.

In the active area AA, an organic layer 250 may be disposed on the substrate 110 on which the insulating film 125 is disposed.

The organic layer 250 may be disposed to cover the insulating film 125.

Although not illustrated in FIG. 2, the organic layer 250 may have a multi-layer structure and may include at least one light emitting layer. The organic layer 250 emits a light of same color.

The second electrode 260 of the organic light emitting device OLED may be disposed to cover the organic layer 250.

Such a second electrode 260 may contain a metal having reflectivity.

For example, the second electrode 260 may contain a metal such as aluminum (Al), molybdenum (Mo), copper (Cu), or silver (Ag) or an alloy such as molybdenum titanium (MoTi). However, the present disclosure is not limited thereto.

The organic layer 250 and the second electrode 260 may be arranged over the entire face of the active area AA. However, the present disclosure is not limited thereto.

The electronic device 100 according to an aspect of the present disclosure may be a bottom emission type in which light generated from the organic layer 250 is emitted in a direction towards the substrate 110.

An encapsulation member 190 that can prevent penetration of moisture and a foreign material into the organic light emitting device OLED may be disposed on the second electrode 260.

In the active area AA, the electronic device 100 may include a first light emission area EA1 and a first non-light emission area NEA1.

The first light emission area EA1 may be an area corresponding to an area not overlapping with the insulating film 125. The first non-light emission area NEA1 may be an area corresponding to an area in which the insulating film 125 is disposed.

In an aspect of the present disclosure, the substrate 110 may include a plurality of protrusions 211 integrally formed on the rear face of the substrate 110.

In FIG. 2, although each of the plurality of protrusions 211 is illustrated to have a configuration of a semi-circular shape in a cross-sectional image, the present disclosure is not limited thereto. For example, a sectional shape of each of the plurality of protrusions 211 may be an oval shape or a polygonal shape. In addition, the sectional shapes of at least two protrusions 211 disposed in the active area AA may be different from each other.

The plurality of protrusions 211 can perform the role of inhibiting a phenomenon in which light L emitted from the organic light emitting device OLED is trapped inside the electronic device 100 and is not extracted to the outside of the electronic device 100.

More specifically, light L emitted from the organic light emitting device OLED is directed toward the substrate 110. The surface of the protrusions 211 formed on the substrate 110 has a slope with respect to a direction in which the substrate 110 extends (horizontal direction).

The slope of the surface of such protrusions 211 can induce refraction of light, and light trapped inside the electronic device 100 can be extracted to the outside of the electronic device 100 through this.

The surface of the plurality of protrusions 211 may have an angle formed with respect to the horizontal plane to be 40 degrees to 60 degrees or an angle formed with respect to the horizontal plane to be 120 degrees to 140 degrees. However, the present disclosure is not limited thereto.

A wavelength converting layer 280 may be disposed on the rear face of the substrate 110 including the plurality of protrusions 211. The wavelength converting layer 280 can perform the role of converting the wavelength of light emitted from the organic light emitting device OLED.

The light L emitted from the organic light emitting device OLED may be blue light or green light, and light extracted to the outside of the electronic device 100 through the wavelength converting layer 280 may have a wavelength of 600 nm to 850 nm.

The wavelength converting layer 280 may be attached to the rear face of the substrate 110 through an adhesion layer 270.

The light emitted from the organic light emitting device OLED can pass through the adhesion layer 270 and be extracted to the outside of the electronic device 100. The adhesion layer 270 may be formed using a transparent organic material for preventing absorption of a large amount of light in the adhesion layer 270. However, the present disclosure is not limited thereto.

The wavelength converting layer 280 may be included in the active area AA.

Such a wavelength converting layer 280 may include a first wavelength conversion area 281, a second wavelength conversion area 282, and a third wavelength conversion area 283 that are disposed to be separate from each other.

Each of the first wavelength conversion area 281, the second wavelength conversion area 282, and the third wavelength conversion area 283 can convert light L emitted from the organic light emitting device OLED into light having different wavelength.

The wavelength of light extracted to the outside of the electronic device 100 through the first wavelength conversion area 281, the second wavelength conversion area 282, and the third wavelength conversion area 283 may be 600 nm to 850 nm.

In addition, a wavelength at which a maximum peak of light that has passed through the first wavelength conversion area 281 appears may be shorter than a wavelength at which a maximum peak of light that has passed through the second wavelength conversion area 282 or the third wavelength conversion area 283 appears.

A wavelength at which a maximum peak of light that has passed through the second wavelength conversion area 282 appears may be shorter than a wavelength at which a maximum peak of light that has passed through the third wavelength conversion area 283 appears.

For example, the light that has passed through the first wavelength conversion area 281 has a wavelength of 600 nm to 680 nm, and a wavelength represented by the maximum peak thereof may be 630 nm. However, the present disclosure is not limited thereto.

The light that has passed through the second wavelength conversion area 282 has a wavelength that is longer than 680 nm and is equal to or shorter than 780 nm, and a wavelength represented by the maximum peak thereof may be 730 nm. However, the present disclosure is not limited thereto.

The light that has passed through the third wavelength conversion area 283 has a wavelength that is longer than 780 nm and is equal to or shorter than 850 nm, and a wavelength represented by the maximum peak thereof may be 830 nm. However, the present disclosure is not limited thereto.

To sum up, the light that has passed through the first wavelength conversion area 281 may be red light, and the light that has passed through the second wavelength conversion area 282 may also be red light that has a wavelength longer than that of the light that has passed through the first wavelength conversion area 281. In addition, the light that has passed through the third wavelength conversion area 283 may be infrared light.

The first to third wavelength conversion areas 281, 282, and 283 may have a structure in which a plurality of wavelength converting particles 286a, 287a, and 288a are respectively dispersed in resin layers 286, 287, and 288.

More specifically, the first wavelength conversion area 281 may have a structure in which a plurality of first wavelength converting particles 286a is dispersed in a first resin layer 286. Here, the plurality of first wavelength converting particles 286a can convert the wavelength of light L emitted from the organic light emitting device OLED into a wavelength of 600 nm to 680 nm. However, the present disclosure is not limited thereto.

The second wavelength conversion area 282 may have a structure in which a plurality of second wavelength converting particles 287a is dispersed in a second resin layer 287. Here, the plurality of second wavelength converting particles 287a can convert the wavelength of light L emitted from the organic light emitting device OLED into a wavelength that is longer than 680 nm and is equal to or shorter than 780 nm. However, the present disclosure is not limited thereto.

The third wavelength conversion area 283 may have a structure in which a plurality of third wavelength converting particles 288a is dispersed in a third resin layer 288. Here, the plurality of third wavelength converting particles 288a can convert the wavelength of light L emitted from the organic light emitting device OLED into a wavelength that is longer than 780 nm and is equal to or shorter than 850 nm. However, the present disclosure is not limited thereto.

The first to third wavelength converting particles 286a, 287a, and 288a may be quantum dots.

For example, each of the first to third wavelength converting particles 286a, 287a, and 288a may be independently selected from a group composed of CdS, CdSe, CdTe, ZnS, ZnSe, ZnTe, ZnO, CdSeS, CdSeTe, CdSTe, ZnSeS, ZnSeTe, ZnSTe, CdZnS, CdZnSe, CdZnTe, CdZnSeS, CdZnSeTe, CdZnSTe, GaN, GaP, GaAs, AN, AlP, AlAs, InN, InP, InAs, GaNP, GaNAs, GaPAs, AlNP, AlNAs, AlPAs, InNP, InNAs, InPAs, GaAlNP, GaAlNAs, GaAlPAs, GaInNP, GaInNAs, GaInPAs, InAlNP, InAlNAs, InAlPAs, CdSe—ZnS, InP—ZnS, and combinations thereof. However, the present disclosure is not limited thereto.

As the first to third wavelength converting particles 286a, 287a, 288a, different materials may be selected, and sizes of particles may be different from each other.

As described above, the light L emitted from the organic light emitting device OLED may be blue light or green light. However, the present disclosure is not limited thereto. As the light L emitted from the organic light emitting device OLED, light having a wavelength shorter than the wavelength of light converted by the first to third wavelength conversion areas 281, 282, and 283 is sufficient.

In other words, the wavelength of the light L emitted from the organic light emitting device OLED may be shorter than 600 nm. However, the present disclosure is not limited thereto.

The wavelength of the light L emitted from the organic light emitting device OLED being shorter than the wavelengths converted by the first to third wavelength conversion areas 281, 282, and 283 represents that the energy of the light L emitted from the organic light emitting device OLED is higher than the energy of light converted by the first to third wavelength conversion areas 281, 282, and 283.

Since transfer from a high-energy side to a low-energy side has efficiency higher than transfer from a low-energy side to a high-energy side, a light loss can be minimized in the process of converting the wavelength of the light L emitted from the organic light emitting device OLED using the first to third wavelength conversion areas 281, 282, and 283.

In the electronic device 100 according to an aspect of the present disclosure, light L emitted from the organic light emitting device OLED, after passing through the substrate 110 and the adhesion layer 270, can be extracted to the outside of the electronic device 100 through the first wavelength conversion area 281, the second wavelength conversion area 282, or the third wavelength conversion area 283.

Meanwhile, in a case in which the electronic device according to an aspect of the present disclosure is a cosmetic device or a treatment device including the organic light emitting device OLED, light emitted from the first to third wavelength conversion areas 281, 282, and 283 may penetrate into the skin of a person.

Since the wavelengths of light emitted from the first to third wavelength conversion areas 281, 282, and 283 of the wavelength converting layer 280 are different from each other, depths up to which the light penetrates into the skin may be different.

This will be reviewed as below with reference to FIG. 3.

Figure 3:
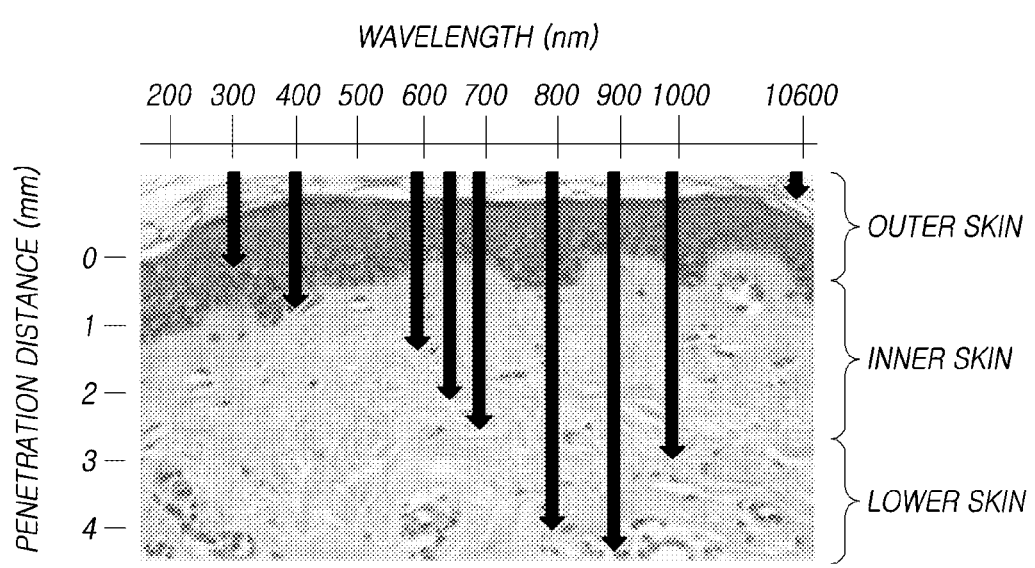
FIG. 3 is a diagram illustrating a penetration depth for a user's skin for each wavelength of light.

FIG. 3 is a diagram illustrating a penetration depth for a user's skin for each wavelength of light.

Referring to FIG. 3, light having a wavelength of about 600 nm to 700 nm can penetrate through outer skin and into inner skin of people skin. In addition, light having a wavelength of about 800 nm can penetrate through outer skin, inner skin, and into lower skin (subcutaneous tissues) of people skin.

Light having a wavelength of 630 nm to 830 nm is a main light for acquiring effects of inflammation treatments and skin regeneration through penetration into inner skin and lower skin.

The light extracted to the outside of the electronic device 100 according to an aspect of the present disclosure has a wavelength of 600 nm to 850 nm, and accordingly, in a case in which the electronic device 100 is used as a cosmetic device or a treatment device including an organic light emitting device OLED, remarkable effects can be acquired in the fields of inflammation treatments and skin regeneration.

While the wavelength of effective light is different in accordance with skin thicknesses of ethnic groups and individuals, light extracted from the electronic device 100 according to an aspect of the present disclosure has a broad wavelength band (600 nm to 850 nm), and accordingly, a deviation of effects for inflammation treatments and skin regeneration according to an ethnic group and a skin thickness also can decrease.

In other words, effects of inflammation treatments and skin regeneration can be acquired regardless of a skin thickness that is different for each ethnic group and each user.

In addition, by providing the electronic device 100 emitting light having a wavelength equal to or longer than 780 nm using the organic light emitting device OLED, when the electronic device 100 according to an aspect of the present disclosure is used, skin treatments and skin regeneration can be smoothly performed.

Particularly, while a general cosmetic or treatment device emits only light having a red wavelength band for skin regeneration, the electronic device 100 according to an aspect of the present disclosure emits light having an infrared wavelength band and accordingly, may have an advantage for skin regeneration.

In the electronic device 100 illustrated in FIG. 2, the refractive index of the organic light emitting device OLED and the refractive index of the substrate 110 may be similar to each other, or the refractive index of the substrate 110 may be higher than the refractive index of the organic light emitting device OLED.

For example, the refractive index of the organic light emitting device OLED may be 1.6 to 1.9, the refractive index of the substrate 110 may be 1.6 to 1.9, and, as another example, the refractive index of the substrate 110 may be equal to or higher than 1.7. However, the present disclosure is not limited thereto.

The refractive index of the buffer layer 220 may be 1.6 to 1.9 as well, and the present disclosure is not limited thereto.

Accordingly, the light L emitted from the organic light emitting device OLED can be extracted to the outside of the substrate 110 without being trapped inside the substrate 110 and the organic light emitting device OLED.

In addition, the refractive index of the substrate 110 may be similar to the refractive indexes of the adhesion layer 270 and the first to third resin layers 286, 287, and 288 of the wavelength converting layer 280.

Accordingly, light L emitted from the organic light emitting device OLED passes through the substrate 110 and can be extracted to the outside of the electronic device 100 without being trapped inside the adhesion layer 270 and the wavelength converting layer 280.

Meanwhile, the refractive index of each of the first wavelength converting particles 286a included in the first wavelength conversion area 281, the second wavelength converting particles 287a included in the second wavelength conversion area 282, and the third wavelength converting particles 288a included in the third wavelength conversion area 283 may be 1.6 to 2.0.

Here, the refractive index of the first to third wavelength converting particles 286a, 287a, and 288a may be set such that an absolute value acquired by subtracting the refractive index of the first to third wavelength converting particles 286a, 287a, and 288a from the refractive index of the substrate 110 is equal to or smaller than 0.2.

In a case in which an absolute value acquired by subtracting the refractive index of the first to third wavelength converting particles 286a, 287a, and 288a from the refractive index of the substrate 110 exceeds 0.2, light provided from the organic light emitting device OLED is not extracted to the outside of the electronic device 100 and may be trapped inside the wavelength converting layer 380.

The refractive index may be changed in accordance with materials of the first to third wavelength converting particles 286a, 287a, and 288a, and, in a case in which the refractive index of the first to third wavelength converting particles 286a, 287a, 288a is higher than the refractive index of the first to third resin layers 286, 287, and 288, the first to third resin layers 286, 287, and 288 may further include scattering particles.

The scattering particles causes the light L emitted from the organic light emitting device OLED to be able to be extracted to the outside of the electronic device 100 without being trapped inside the wavelength converting layer.

The wavelength converting layer 280 may include at least one partition wall 285 disposed between different wavelength converting areas.

For example, partition walls 285 may be disposed between the first wavelength conversion area 281 and the second wavelength conversion area 282, between the second wavelength conversion area 282 and the third wavelength conversion area 283, and between the third wavelength conversion area 283 and the first wavelength conversion area 281.

The partition wall 285 can perform the role of causing light incident to the first to third wavelength conversion areas 281, 282, and 283 not to go into another wavelength conversion area adjacent to the wavelength conversion area to which the light has been incident. Accordingly, a light loss according to mutual interference can be minimized.

Such a partition wall 285 may have a refractive index lower than the refractive index of the substrate 110. For example, the refractive index of the partition wall 285 may be equal to or lower than 1.5. However, the present disclosure is not limited thereto.

In this way, by configuring the refractive index of the partition wall 285 to be lower than the refractive index of the first to third wavelength conversion areas 281, 282, and 283, light incident in a direction towards the partition wall 285 in the first to third wavelength conversion areas 281, 282, and 283 is trapped inside the first to third wavelength conversion areas 281, 282, and 283 and cannot go into another wavelength conversion area adjacent thereto.

A height H2 of such a partition wall 285 may be higher than a thickness H1 of the first to third wavelength conversion areas 281, 282, and 283. Here, the height H2 of the partition wall 285 and the thickness H1 of the first to third wavelength conversion areas 281, 282, and 283 may be shortest lengths between two surfaces of the partition wall 285 and between the two surfaces of the first to third wavelength conversion areas 281, 282, and 283 with reference to a direction (vertical direction) in which components of the organic light emitting device OLED are stacked on the surface of the substrate 110.

In FIG. 2, although a configuration in which the thickness H1 of the first to third wavelength conversion areas 281, 282, and 283 correspond to each other is illustrated, the present disclosure is not limited thereto, and the thicknesses of the first to third wavelength conversion areas 281, 282, and 283 may be different from each other. In an aspect of the present disclosure, the thickness of each of the first to third wavelength conversion areas 281, 282, and 283 may be configured to be lower than the height H2 of the partition wall 285.

By configuring the height H2 of the partition wall 285 to be higher than the thickness H1 of the first to third wavelength conversion areas 281, 282, and 283, it can be prevented that the materials of the first to third resin layers 286, 287, and 288 and the particles of the first to third wavelength converting particles 286a, 287a, 288a flow over the partition wall 285 and penetrate into mutually-different wavelength conversion areas at the time of manufacturing the wavelength converting layer 280.

The first wavelength conversion area 281 may correspond to the second light emission area EA2 of the electronic device 100, the second wavelength conversion area 282 may correspond to the third light emission area EA3 of the electronic device 100, and the third wavelength conversion area 283 may correspond to the fourth light emission area EA4 of the electronic device 100

A second non-light emission area NEA2 may be disposed between the second light emission area EA2 and the third light emission area EA3, between the third light emission area EA3 and the fourth light emission area EA4, and between the fourth light emission area EA4 and the second light emission area EA2. The second non-light emission area NEA2 may be an area corresponding to an area in which the partition wall 285 is disposed.

Each of the second to fourth light emission areas EA2, EA3, and EA4 may also correspond to one first light emission area EA1.

At this time, the area of each of the second to fourth light emission areas EA2, EA3, and EA4 may be larger than the area of the first light emission area EA1.

The reason for this is that, in accordance with diffusion (diffusion according to scattering) according to a plurality of first to third wavelength converting particles 286a, 287a, 288a of the wavelength converting layer 280, light can be emitted in a wide area.

Accordingly, the area of the second to fourth light emission areas EA2, EA3, and EA4 that are substantial areas from which light is emitted to the outside of the electronic device 100 may be larger than the area of the first light emission area EA1.

The structure of the electronic device 100 according to an aspect of the present disclosure is not limited to that illustrated in FIG. 2.

The structure of an electronic device 100 according to another aspect will be reviewed as below with reference to FIG. 4.

Figure 4:
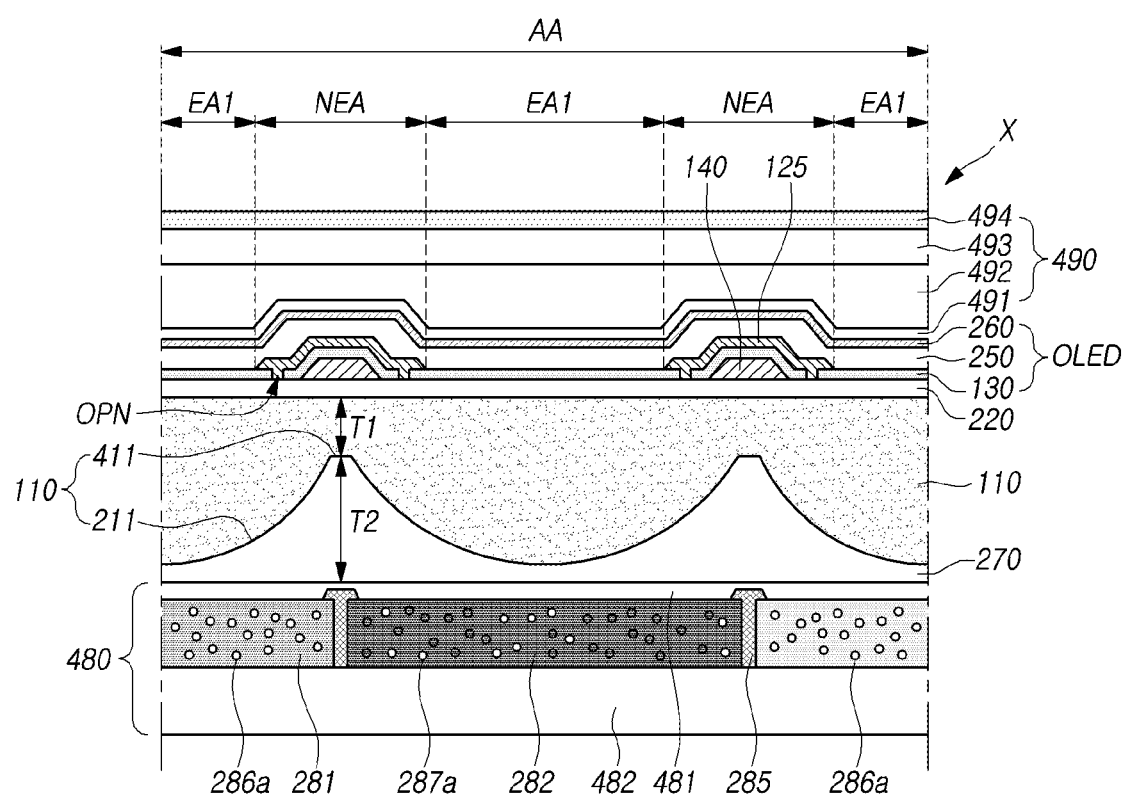
FIG. 4 is a cross-sectional view of an electronic device according to another aspect of the present disclosure.

FIG. 4 is a cross-sectional view of the electronic device according to another aspect.

FIG. 4 illustrates a sectional structure of an area corresponding to the area X illustrated in FIG. 1A, and taken along line I-I' of FIG. 1B.

In the following description, details (configurations, effects, and the like) that are the same as those of the aspects described above may be omitted.

Referring to FIG. 4, in the electronic device 100 according to another aspect of the present disclosure, as illustrated in FIG. 2, an auxiliary electrode 140, an insulating film 125, and an organic light emitting device OLED may be disposed on a substrate 110.

An encapsulation member 490 may be disposed on a second electrode 260 of the organic light emitting device OLED.

The encapsulation member 490 may include a capping layer 491, an encapsulation layer 492, an adhesion layer 493, and a metal film 494.

The capping layer 491 may be disposed on the second electrode 260 of the organic light emitting device OLED. The capping layer 491 may be disposed to cover the second electrode 260.

The capping layer 491 is a component for performing the role of protecting the second electrode 260 of the organic light emitting device OLED and may be configured as a single layer composed of an organic material. However, the present disclosure is not limited thereto. For example, the capping layer 491 may contain an inorganic material and may be composed of multiple layers.

The encapsulation layer 492 may be disposed on the capping layer 491. The encapsulation layer 492 may be disposed to cover the capping layer 491.

Such an encapsulation layer 492 may be composed of an inorganic material such as SiOx or SiNx. However, the present disclosure is not limited thereto. In addition, although a configuration in which the encapsulation layer 492 is a single layer is illustrated in FIG. 4, the encapsulation layer 492 may be composed of multiple layers. In such a case, the encapsulation layer 492 may have a configuration in which an inorganic film and an organic film are alternately disposed. However, the present disclosure is not limited thereto.

The adhesion layer 493 may be disposed on the encapsulation layer 492. The adhesion layer 493 may be disposed to cover the encapsulation layer 492. In addition, the adhesion layer 493 may further contain a moisture absorbent and the like.

The metal film 494 may be disposed on the adhesion layer 493.

The adhesion layer 493 has the role of bonding the metal film 494 disposed on the adhesion layer 493 to the substrate 110 in which the encapsulation layer 492 is disposed and can prevent penetration of moisture or a foreign material into the organic light emitting device OLED.

The substrate 110 may include a plurality of protrusions 211 that are integrally formed on the rear face of the substrate 110 in an active area AA.

More specifically, the substrate 110 may include a connection part 411 connecting one protrusion 211 and another protrusion 211 adjacent thereto.

The surface of the plurality of protrusions 211 may have an angle formed with respect to the horizontal plane to be 40 degrees to 60 degrees or may have an angle formed with respect to the horizontal plane to be 120 degrees to 140 degrees. However, the present disclosure is not limited thereto.

On the other hand, the surface of the connection part 411 of the substrate 110 may have an angle formed with respect to the horizontal plane not to be 40 degrees to 60 degrees or 120 degrees to 140 degrees.

Accordingly, a probability of occurrence of total reflection of light emitted from organic light emitting device OLED in the connection part 411 of the substrate 110 may be very high. In other words, in an area corresponding to the connection part 411 of the substrate 110, the amount of extracted light may be smaller than in an area corresponding to the protrusions 211 of the substrate 110.

In an area corresponding to the connection part 411, the substrate 110 may have a minimum thickness T1. Here, the thickness of the substrate 110 may be a shortest length between the two surfaces of the substrate 110 with respect to a direction (the vertical direction) in which components of the organic light emitting device OLED are stacked on the surface of the substrate 110.

In the active area AA, the connection part 411 of the substrate 110 may overlap with an area in which the insulating film 125 is disposed on the substrate 110.

In other words, an area in which the substrate 110 has the minimum thickness T1 (in other words, an area corresponding to the connection part) may overlap with the first non-light emission area NEA1.

In other words, the connection part 411 of the substrate 110 may be disposed between one first light emission area EA1 and another first light emission area EA1 adjacent thereto.

For example, when the connection part 411 is disposed in an area corresponding to the first non-light emission area NEA1, the connection part 411 is an area that can induce total reflection of light emitted from the organic light emitting device OLED, and accordingly, the amount of light extracted in a direction towards the wavelength converting layer 480 may be small.

Accordingly, one protrusion 211 may correspond to one first light emission area EA1. However, the present disclosure is not limited thereto, and two or more protrusions 211 may overlap with one first light emission area EA1 depending on the situations.

An adhesion layer 270 may be disposed on the rear face of such a substrate 110.

An area in which the adhesion layer 270 has the maximum thickness T2 may be an area corresponding to the connection part 411 of the substrate 110.

The adhesion layer 270 may perform the role of bonding the substrate 110 in which the organic light emitting device OLED is disposed and a wavelength converting layer 480 together.

In this aspect, the wavelength converting layer 480 may include a first wavelength conversion area 281, a second wavelength conversion area 282, a third wavelength conversion area 283, a partition wall 285, a barrier layer 481, and a buffer layer 482.

The barrier layer 481 may be configured to be bonded to the adhesion layer 270.

The barrier layer 481 can perform the role of preventing penetration of moisture into the organic light emitting device OLED.

The buffer layer 482 may be disposed on the rear face of the first to third wavelength conversion areas 281, 282, and 283. The buffer layer 482 may perform the role of supporting the first to third wavelength conversion areas 281, 282, and 283 and the partition wall 285, and preventing penetration of moisture into first to third wavelength converting particles 286a, 287a, and 288a respectively included in the first to third wavelength conversion areas 281, 282, and 283.

Next, a method of manufacturing the electronic device 100 according to an aspect of the present disclosure will be reviewed as below with reference to FIGS. 5 to 10.

FIGS. 5 to 10 are diagrams schematically illustrating a method of manufacturing an electronic device according to an aspect of the present disclosure.

In the following description, details (configuration, effects, and the like) that are the same as those of the aspects described above may be omitted.

Figure 5:
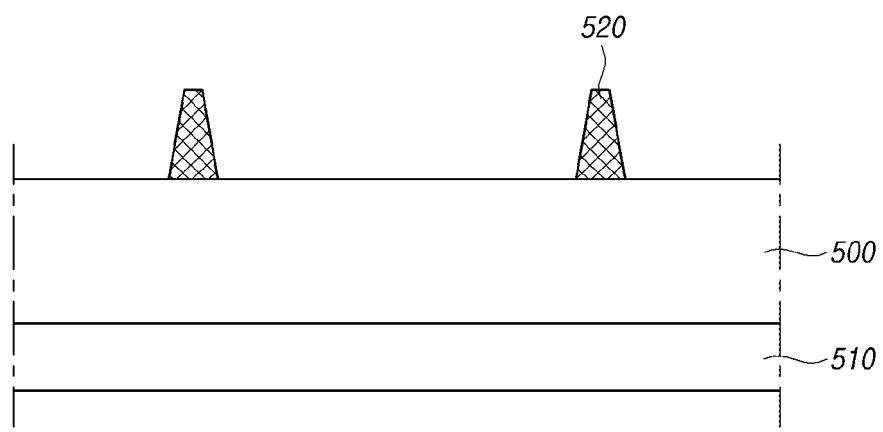
FIGS. 5 to 10 are diagrams schematically illustrating a method of manufacturing an electronic device according to an aspect of the present disclosure.

Referring to FIG. 5, a sacrificial layer 500 may be disposed on a sacrificial substrate 510. A patterned photoresist 520 may be disposed on the sacrificial layer 500.

Here, the sacrificial substrate 510 may be a glass substrate. However, the present disclosure is not limited thereto.

The sacrificial layer 500 may be composed of a material that can be patterned through a photolithography process.

In a state in which the patterned photoresist 520 is disposed illustrated in FIG. 5, the sacrificial layer 500 can be patterned through the photolithography process.

Figure 6:
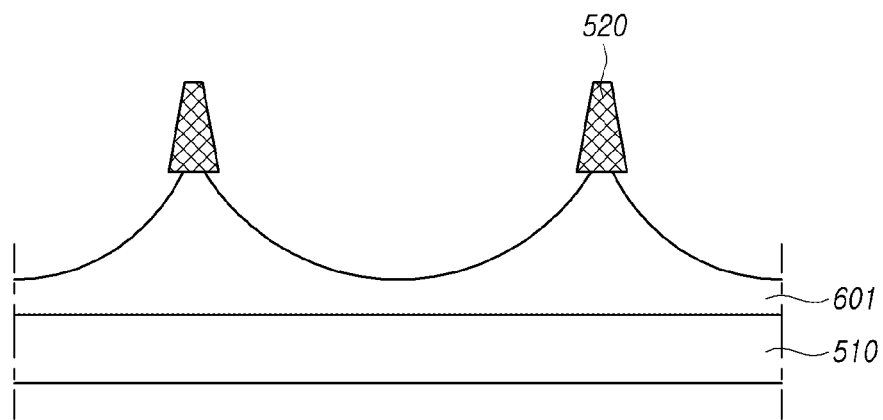

When the sacrificial layer 500 is pattern, as illustrated in FIG. 6, a sacrificial layer 601 in an area in which the photoresist 520 is not disposed may be etched, and a sacrificial layer 601 in an area in which the photoresist 520 is disposed may not be etched.

In the sacrificial layer 601 that has been patterned through the photolithography process, a plurality of concave parts 602 and a connection part 603 of the sacrificial layer 601 connecting the plurality of concave parts 602 may be formed.

Figure 8:
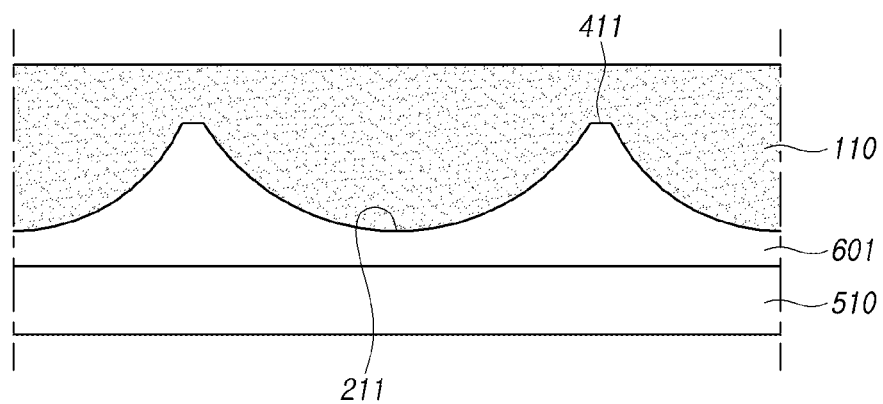

Thereafter, as illustrated in FIG. 8, a substrate 110 may be disposed on the sacrificial layer 601.

The substrate 110 may be formed along the morphology of the patterned sacrificial layer 601.

Figure 7:
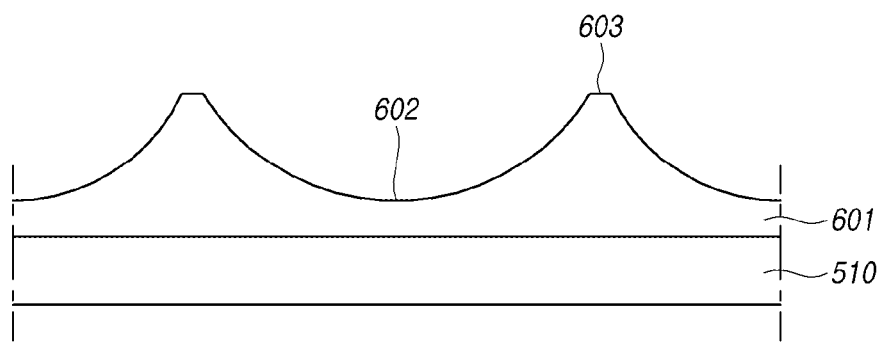

More specifically, referring to FIGS. 7 and 8, in an area corresponding to the concave part 602 of the sacrificial layer 601, protrusions 211 of the substrate 110 may be formed. Then, in an area corresponding to the connection part 603 of the sacrificial layer 601, a connection part 411 of the substrate 110 may be formed.

Figure 9:
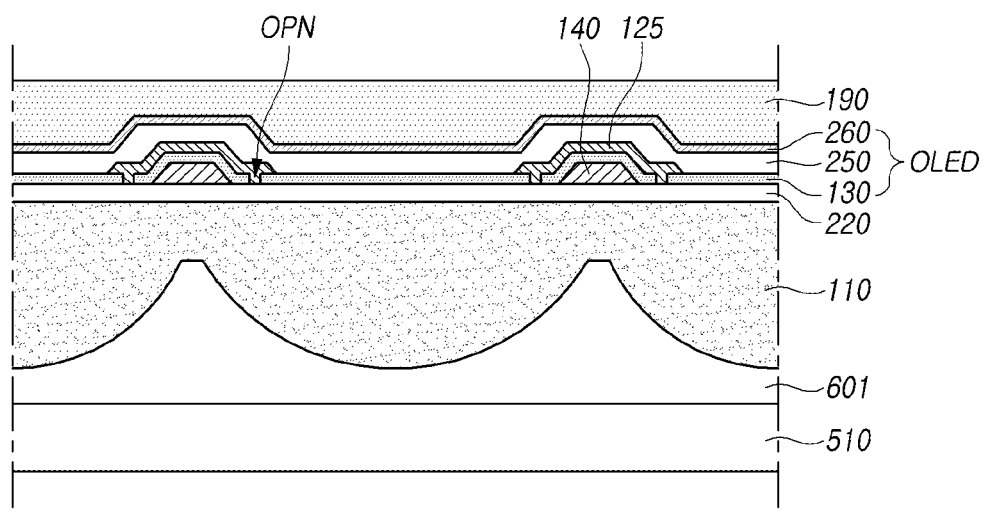

Thereafter, as illustrated in FIG. 9, on the substrate 110 on which a plurality of the protrusions 211 and the connection part 411 are formed, an auxiliary electrode 140, a first electrode 130, an insulating film 125, an organic layer 250, a second electrode 260, and an encapsulation member 190 may be sequentially formed.

In FIG. 9, although the encapsulation member 190 is illustrated to have the structure illustrated in FIG. 2, the present disclosure is not limited thereto. For example, the encapsulation member 490 illustrated in FIG. 4 may be also disposed on the substrate 110.

Figure 10:
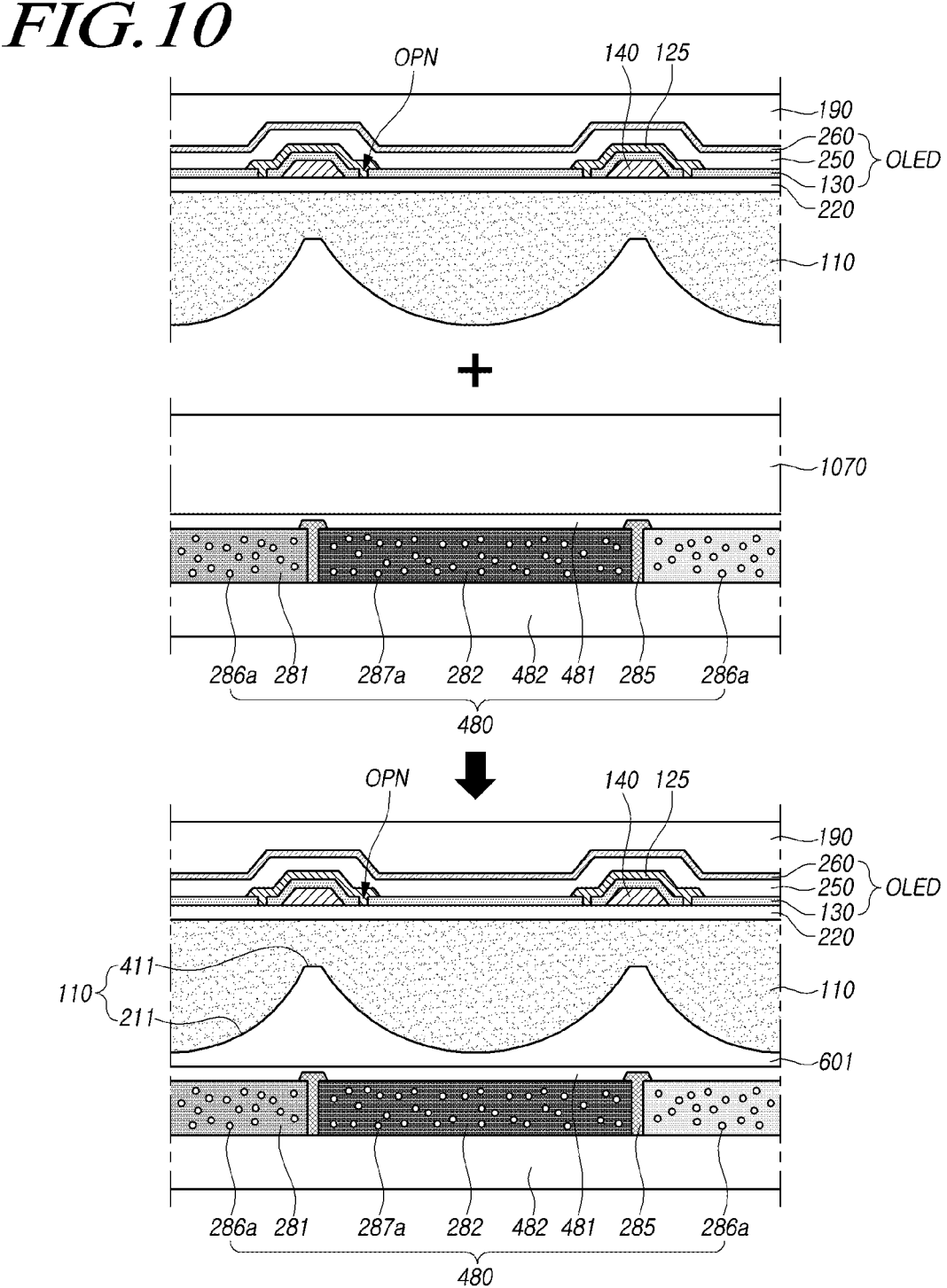

Thereafter, as illustrated in FIG. 10, the sacrificial layer 601 and the sacrificial substrate 510 may be separated from the rear face of the substrate 110 on which the auxiliary electrode 140, the first electrode 130, the insulating film 125, the organic layer 250, the second electrode 260, and the encapsulation member 190 are disposed.

At this time, the sacrificial layer 601 and the sacrificial substrate 510 disposed on the rear face of the substrate 110 may be separated through a process of separating the sacrificial layer 601 and the sacrificial substrate 510 by emitting laser to the rear face of the substrate 110 such as laser lift off. However, the process of separating sacrificial layer 601 and the sacrificial substrate 510 from the substrate 110 is not limited thereto.

An adhesion layer material 1070 and a wavelength converting layer 480 attached to one surface of the adhesion layer material 1070 are attached.

When the adhesion layer material 1070 is attached to the rear face of the substrate 110, an adhesion layer 270 having a shape corresponding to the morphology of the rear surface of the substrate 110 may be formed on a surface on which the adhesion layer material 1070 is brought into contact with the substrate 110.

The adhesion layer 270 may perform the role of attaching the wavelength converting layer 480 to the rear surface of the substrate 110.

In FIG. 10, although the structure of the wavelength converting layer 480 is illustrated to have a structure corresponding to that illustrated in FIG. 4, the present disclosure is not limited thereto. For example, the structure of the wavelength converting layer 480 may be the structure of the wavelength converting layer 280 illustrated in FIG. 2.

Such an electronic device 100 may be a cosmetic device or a treatment device including an organic light emitting device OLED. For example, as illustrated in FIG. 11, the electronic device 100 may be a light output device for skin management or a light output device for skin treatments.

Figure 11:
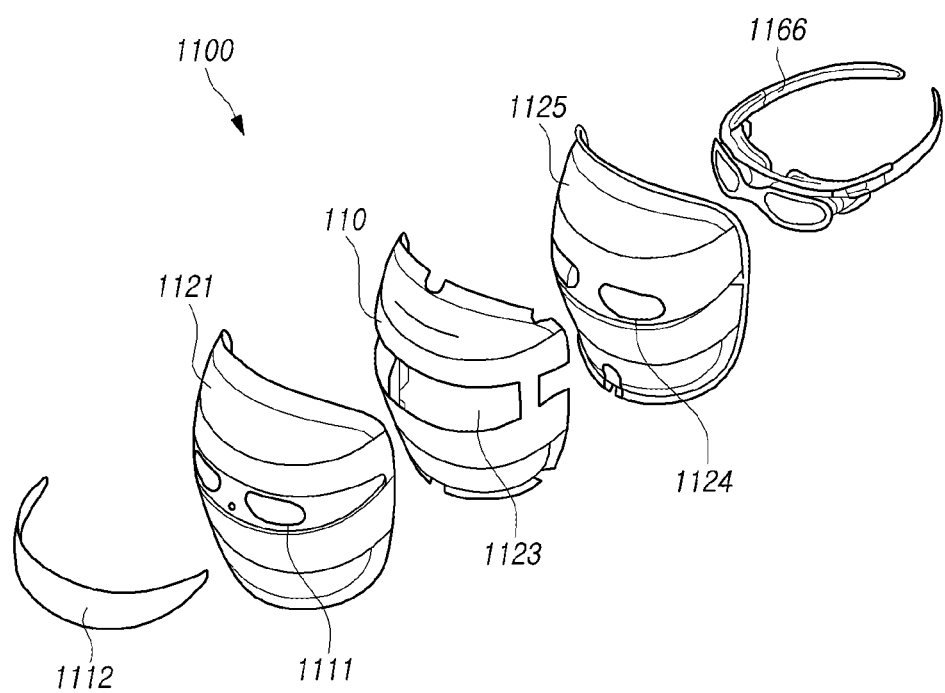
FIG. 11 is a perspective view illustrating the structure of an electronic device according to an aspect of the present disclosure.

FIG. 11 is a perspective view illustrating the structure of an electronic device according to an aspect of the present disclosure.

In the following description, details (configurations, effects, and the like) that are the same as those of the aspects described above may be omitted.

Referring to FIG. 11, an electronic device 1100 according to an aspect of the present disclosure may include a front cover 1121, a substrate 110, a rear cover 1125, and a wearing device 1126.

The front cover 1121 is the front surface of the electronic device 1100 and can protect the substrate 110 disposed between the rear cover 1125 and the front cover 1121 from an external shock, a contact, and the like. For this, the front cover 1121 may be realized using various kinds of plastic, ceramics, and the like. However, the present disclosure is not limited thereto.

In the front cover 1121, an opening 1111 may be formed for securing the field of vision of a user when being worn by the user. When a user wears the electronic device 1100, the eyes of the user are positioned in the opening 1111, and the user can secure the field of vision through the opening 1111.

In order to prevent a contact or collision of a foreign material with the eyes of the user through the opening 1111, an opening protection cover 1112 covering the opening 1111 may be provided depending on the situations. The opening protection cover 1112 may be realized using a transparent material such as acryl or plastic. However, the present disclosure is not limited thereto.

The substrate 110 may be the substrate 110 in which the plurality of protrusions 211 illustrated in FIGS. 2 and 4 are integrally formed. The auxiliary electrode 140, the insulating film 125, the organic light emitting device OLED, and the encapsulation member 190 may be disposed on one surface of the substrate 110, and the adhesion layer 270 and the wavelength converting layers 280 and 480 may be disposed on the other surface of the substrate 110.

Although not illustrated in the drawing, the substrate 110 may include a control unit used for controlling a light output operation of at least one the organic light emitting device OLED. The control unit may be realized by an integrated circuit (IC), a microcomputer, an embedded processor, an application processor (AP), or the like.

In addition, the substrate 110 included in the electronic device 1100 having a mask shape may be formed such that at least a part thereof forms a curved face. The substrate is made of flexible material, and the substrate is bended or folded.

The rear cover 1125 is fastened to the front cover 1121 and the substrate 110 and may be formed to cover one face of the substrate 110. The front cover 1121 and the rear cover 1125 prevent penetration of water and other foreign materials into the substrate 110 disposed therebetween and can prevent malfunctions and damages in an organic light emitting device OLED and other constituent elements disposed on the substrate 110.

In order to allow light emitted from the organic light emitting device OLED disposed in the substrate 110 to be emitted to a user's facial skin, the rear cover 1125 may be realized using a transparent material such as plastic or acryl. In addition, the rear cover 1125 may include an opening 1124 used for securing the field of view of a user.

The wearing device 1126 can fix the electronic device 1100 to a user as the user wears the electronic device 1100. The wearing device 1126 may be fastened to the rear cover 1125. For example, the wearing device 1126 may have a glass shape that can be worn by being settled on the nose and the ears of the user.

Since light extracted to the outside of the electronic device 1100 can be configured to have a wavelength of 600 nm to 850 nm and irradiate a face of a user wearing the electronic device, and the wavelength of the light can penetrate into an inner skin of the user, as shown in FIG. 3, remarkable effects can be acquired in the fields of inflammation treatments and skin regeneration.

In addition, since light extracted from the electronic device 1100 according to an aspect of the present disclosure has a broad wavelength band (600 nm to 850 nm), deviations in the effects of inflammation treatments and skin regeneration according to an ethnic group and a skin thickness can be decreased.

As described above, according to aspects of the present disclosure, an electronic device emitting light of wavelengths from which effects of inflammation treatments and skin regeneration can be acquired can be provided.

According to aspects of the present disclosure, an electronic device from which effects of inflammation treatments and skin regeneration can be acquired regardless of an ethnic group and a user's skin thickness can be provided.

According to aspects of the present disclosure, an electronic device for skin management or skin treatments that includes an organic light emitting device OLED having a long life can be provided.

The above description and the accompanying drawings provide an example of the technical idea of the present disclosure for illustrative purposes only. Those having ordinary knowledge in the technical field, to which the present disclosure pertains, will appreciate that various modifications and changes in form, such as combination, separation, substitution, and change of a configuration, are possible without departing from the essential features of the present disclosure. Therefore, the aspects disclosed in the present disclosure are intended to illustrate the scope of the technical idea of the present disclosure, and the scope of the present disclosure is not limited by the aspect. The scope of the present disclosure shall be construed on the basis of the accompanying claims in such a manner that all of the technical ideas included within the scope equivalent to the claims belong to the present disclosure.

What is claimed is:

1. An electronic device comprising:
   a substrate;
   an auxiliary electrode disposed on the substrate;
   a plurality of light emitting devices disposed on the substrate and emitting a light of same color; and
   a wavelength converting layer disposed on the substrate and converting the light emitted from the light emitting devices,
   wherein the converted light is extracted to outside the electronic device and has a wavelength longer than that of the light emitted from the light emitting devices,
   wherein the plurality of light emitting devices include a first electrode disposed on the auxiliary electrode and the substrate and an insulating film disposed on the auxiliary electrode,
   wherein the wavelength converting layer includes a partition wall disposed between two adjacent wavelength conversion areas among a plurality of wavelength conversion areas and overlapping the insulating film,
   wherein a first non-light emission area is an area corresponding to an area in which the insulating film is disposed and a second non-light emission area is an area corresponding to an area in which the partition wall is disposed,
   wherein the plurality of light emitting devices are disposed on a front face of the substrate, and the wavelength converting layer is attached to a rear face of the substrate,
   wherein the rear face of the substrate is integrally formed with a plurality of protrusions and a connection part connecting one protrusion and another protrusion, and the connection part of the substrate overlaps with the auxiliary electrode, and
   wherein the substrate has a minimum thickness at an area corresponding to the connection part.

2. The electronic device according to claim 1, wherein the converted light emitted from the wavelength converting layer has a wavelength ranging from 600 nm to 850 nm.

3. The electronic device according to claim 1, wherein the wavelength converting layer includes a plurality of wavelength conversion areas that are separated from each other, and
   wherein the converted light emitted from the plurality of wavelength conversion areas has different wavelengths from each other.

4. The electronic device according to claim 3, further comprising a partition wall disposed between two adjacent wavelength conversion areas among the plurality of wavelength conversion areas,
   wherein the partition wall has a height greater than a thickness of the two adjacent wavelength conversion areas.

5. The electronic device according to claim 4, wherein the partition wall has a refractive index lower than that of the two adjacent wavelength conversion areas.

6. The electronic device according to claim 1,
   wherein the plurality of protrusions corresponds to the light emission areas of the plurality of light emitting devices so as to introduce the light emitted from the light emission areas of the plurality of light emitting devices into the wavelength converting layer.

7. The electronic device according to claim 6, further comprising an adhesion layer disposed between the substrate and the wavelength converting layer.

8. The electronic device according to claim 1, wherein the plurality of light emitting devices include:
   the auxiliary electrode having a mesh shape that includes a plurality of open areas,
   the first electrode including at least one open area, wherein each open area of the first electrode is located in one open area of the auxiliary electrode and extending along the edge thereof, such that the part of the first electrode inside the open area thereof and the part of the first electrode outside the open area thereof connect to each other through a narrow path,
   the insulating film leaving the plurality of the open areas of the auxiliary electrode exposed, wherein the insulating film covers the at least one open area of the first electrode,
   an organic layer disposed on the insulating film and the first electrode; and
   a second electrode disposed on the organic layer.

9. The electronic device according to claim 8, wherein the auxiliary electrode includes a metal material, the first electrode includes a transparent conductive material, and the second electrode includes a reflective metal.

10. The electronic device according to claim 8, wherein the wavelength converting layer includes a plurality of wavelength conversion areas that are separated from each other, the converted light emitted from the plurality of wavelength conversion areas has different wavelengths, wherein the plurality of wavelength conversion areas respectively corresponds to a plurality of light emission areas of the organic layer.

11. The electronic device according to claim 10, wherein each of the wavelength conversion areas is larger than each of the light emission areas of the organic layer.

12. The electronic device according to claim 8, wherein the plurality of light emitting devices are disposed on a front face of the substrate, and the wavelength converting layer is attached to a rear face of the substrate, wherein the rear face of the substrate is integrally formed with a plurality of protrusions, and the plurality of protrusions corresponds to the light emission areas of the organic layers of the plurality of light emitting devices so as to introduce the light emitted from the light emission areas of the organic layer of the plurality of light emitting devices into the wavelength converting layer.

13. The electronic device according to claim 1, wherein the substrate is formed with a mask shape that has at least a part thereof forms a curved face.

14. The electronic device according to claim 13, further comprising a front cover and a rear cover, formed with a mask shape that matches the mask shape of the substrate, wherein the substrate, the plurality of light emitting devices and the wavelength converting layer disposed on the substrate are disposed between a front cover and a rear cover.

15. The electronic device according to claim 14, further comprising a wearing device, fastened to the rear cover.

16. The electronic device according to claim 13, wherein the converted light coming from the wavelength converting layer irradiates a face of a user wearing the electronic device.

17. The electronic device of claim 1, wherein the wavelength of the converted light can penetrate into an inner skin of a user.

18. The electronic device of claim 1, wherein the substrate is made of flexible material that is bendable or foldable.

19. The electronic device according to claim 1, wherein the electronic device is used for skin cosmetics or skin treatments.

* * * * *